(12) United States Patent
Mishima et al.

(10) Patent No.: US 7,503,911 B2
(45) Date of Patent: Mar. 17, 2009

(54) DISPOSABLE WEARING ARTICLE

(75) Inventors: Yoshitaka Mishima, Kagawa-ken (JP);
Taiji Shimakawa, Kagawa-ken (JP);
Kaiyo Nakajima, Kagawa-ken (JP);
Tomoko Sugito, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 296 days.

(21) Appl. No.: 10/690,817

(22) Filed: Oct. 23, 2003

(65) Prior Publication Data

US 2004/0138638 A1  Jul. 15, 2004

(30) Foreign Application Priority Data

Oct. 25, 2002  (JP)  ............... 2002-311678

(51) Int. Cl.
*A61F 13/15* (2006.01)

(52) U.S. Cl. .............. 604/385.19; 604/348; 604/385.14

(58) Field of Classification Search ............ 604/385.19, 604/385.15, 385.14, 385.12, 347–348, 349–354
See application file for complete search history.

(56) References Cited

U.S. PATENT DOCUMENTS

| 3,532,093 | A |  | 10/1970 | Lovret |  |
| 3,858,584 | A |  | 1/1975 | Johnson |  |
| 4,857,064 | A | * | 8/1989 | Mendoza | 604/347 |
| 4,886,508 | A | * | 12/1989 | Washington | 604/327 |
| 5,342,583 | A | * | 8/1994 | Son | 422/107 |
| 6,007,524 | A | * | 12/1999 | Schneider | 604/327 |
| 6,168,584 | B1 | * | 1/2001 | Allen et al. | 604/385.19 |
| 6,183,458 | B1 | * | 2/2001 | Ahlstrand et al. | 604/385.19 |
| 6,464,673 | B1 |  | 10/2002 | Ben Natan |  |
| 6,641,567 | B1 | * | 11/2003 | Williams | 604/327 |
| 6,808,516 | B2 | * | 10/2004 | Tsuji et al. | 604/385.25 |
| 6,840,925 | B2 | * | 1/2005 | Mishima et al. | 604/385.01 |

FOREIGN PATENT DOCUMENTS

| EP | 1174102 | 1/2002 |
| EP | 1219270 | 7/2002 |
| EP | 12432337 | 9/2002 |
| JP | 2523711 | 10/1996 |
| JP | 2002-263134 | 9/2002 |
| WO | 98/43574 | 10/1998 |

\* cited by examiner

*Primary Examiner*—Tatyana Zalukaeva
*Assistant Examiner*—Lynne Anderson
(74) *Attorney, Agent, or Firm*—Lowe Hauptman Ham & Berner, LLP

(57) ABSTRACT

A disposable wearing article includes a holder member which is composed of a front waist region, a rear waist region and a crotch region and a bodily discharge receiving member. The holder member is formed with a through-hole in the crotch region while the receiving member has a protrusion adapted to be inserted into the through-hole from the outer side of the wearing article and to define a concavity which can receive and retain bodily discharges.

10 Claims, 5 Drawing Sheets

DISPOSABLE WEARING ARTICLE

RELATED APPLICATIONS

The present application is based on, and claims priority from, Japanese Application Serial Number 2002-311678, filed Oct. 25, 2002, the disclosure of which is hereby incorporated by reference herein in its entirety

BACKGROUND OF THE INVENTION

The present invention relates to a disposable wearing article such as a disposable diaper for personal care of bodily discharges.

Japanese Utility Model Publication No. 2523711B discloses a disposable diaper provided in a crotch region with a feces receiving concavity and formed around such concavity with a protrusion.

The disposable diaper disclosed in the above-cited Publication is more complicated than a diaper provided with no concavity to receive feces and generally apt to require the correspondingly higher unit cost of the product. From the other viewpoint, this diaper may lead to wasteful use of resources because, even when only the zone of the diaper surrounded by the protrusion has been contaminated with bodily discharges, the remaining zone of the diaper is often substantially free from contamination and the diaper must be thrown away because of such restricted contamination.

SUMMARY OF THE INVENTION

It is an object of the present invention to improve the disposable diaper provided with the concavity adapted to receive bodily discharges such as feces so that the unit cost of such article can be substantially reduced.

According to the present invention, there is provided a disposable wearing article having a front waist region, a rear waist region and a crotch region extending between the waist regions, each having an inner surface facing a wearer's body and an outer surface facing away from the wearer's body, and the crotch region being formed in a transversely middle zone thereof on the inner surface with a protrusion surrounding at least one of an anus and a urethral of the wearer.

The present invention further comprises a holder member having the front waist region, the rear waist regions and the crotch region; and a bodily discharge receiving member detachably held by the holder member; wherein the crotch region is provided in a transversely middle zone thereof with a through-hole extending between the inner surface and the outer surface, and the receiving member comprises an annular portion adapted to be detachably inserted from a side of the outer surface of the holder member into the through-hole so as to form the protrusion and a bursiform portion lying at a side of the outer surface of the holder member and joined to an outer periphery of the annular portion so that bodily discharges flow through the annular portion into the bursiform potion and the receiving member is held by the holder member by detachably joining the receiving member to the holder member around the through-hole.

The present invention includes the following embodiments.

The lateral portions of the holder member in the front and rear waist regions are releasably engaged with each other to define a waist-hole and a pair of leg-holes.

The lateral portions of the holder member in the front and rear waist regions are permanently joined together to define a waist-hole and a pair of the leg-holes.

The protrusion comprises flexible and elastically compressive foamed plastic.

The bursiform portion is formed by a liquid-impervious sheet.

The holder member is washable and reusable.

The holder member is elastically stretchable.

DETAILED DESCRIPTION OF THE PREFERRED EMBODIMENTS

Details of the disposable wearing article according to the present invention will be more fully understood from the description of a disposable diaper as a typical embodiment of the invention given hereunder with reference to the accompanying drawings.

Figure 1:
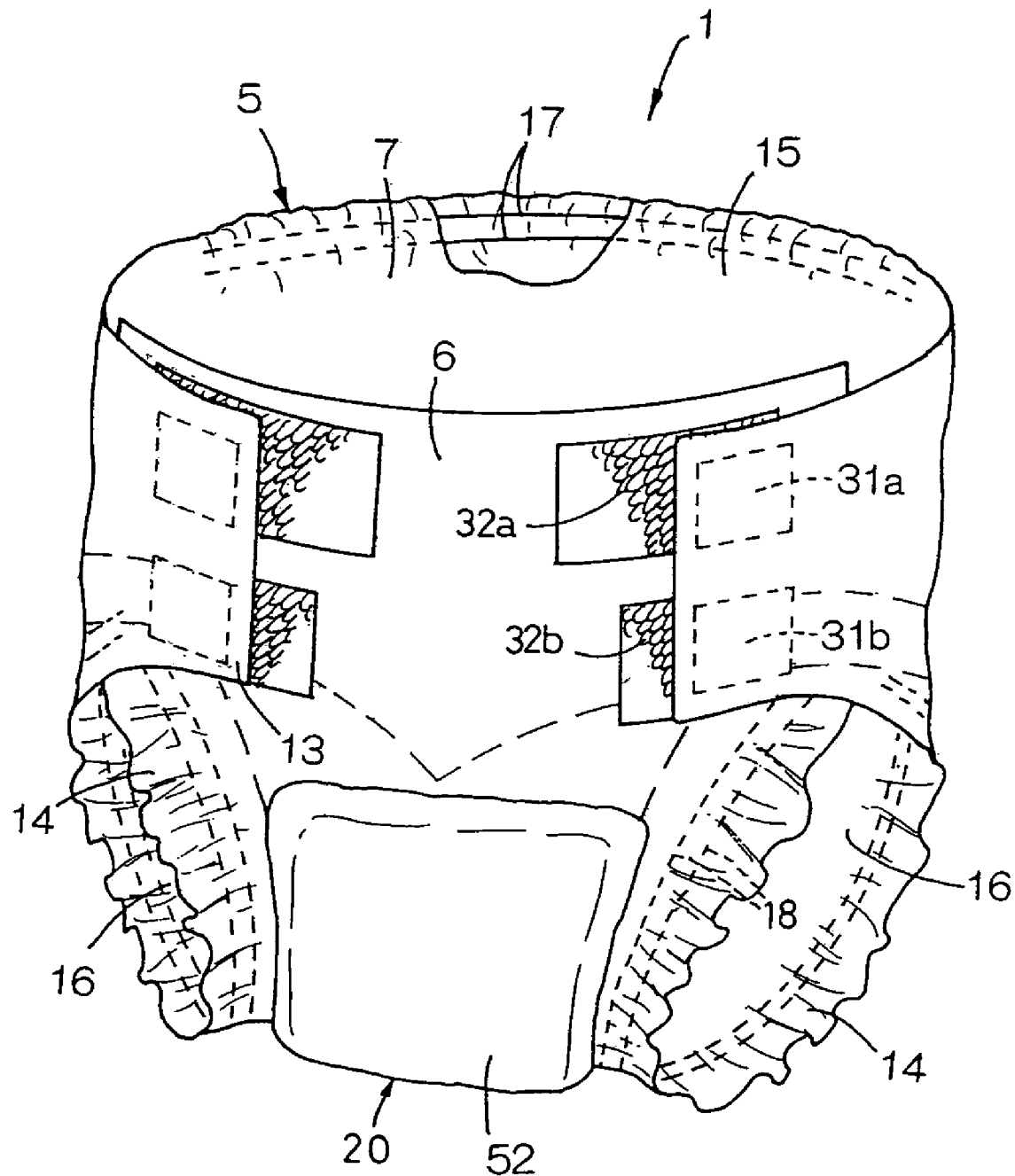
FIG. 1 is a perspective view showing a diaper as put on a wearer's body.
Figure 2:
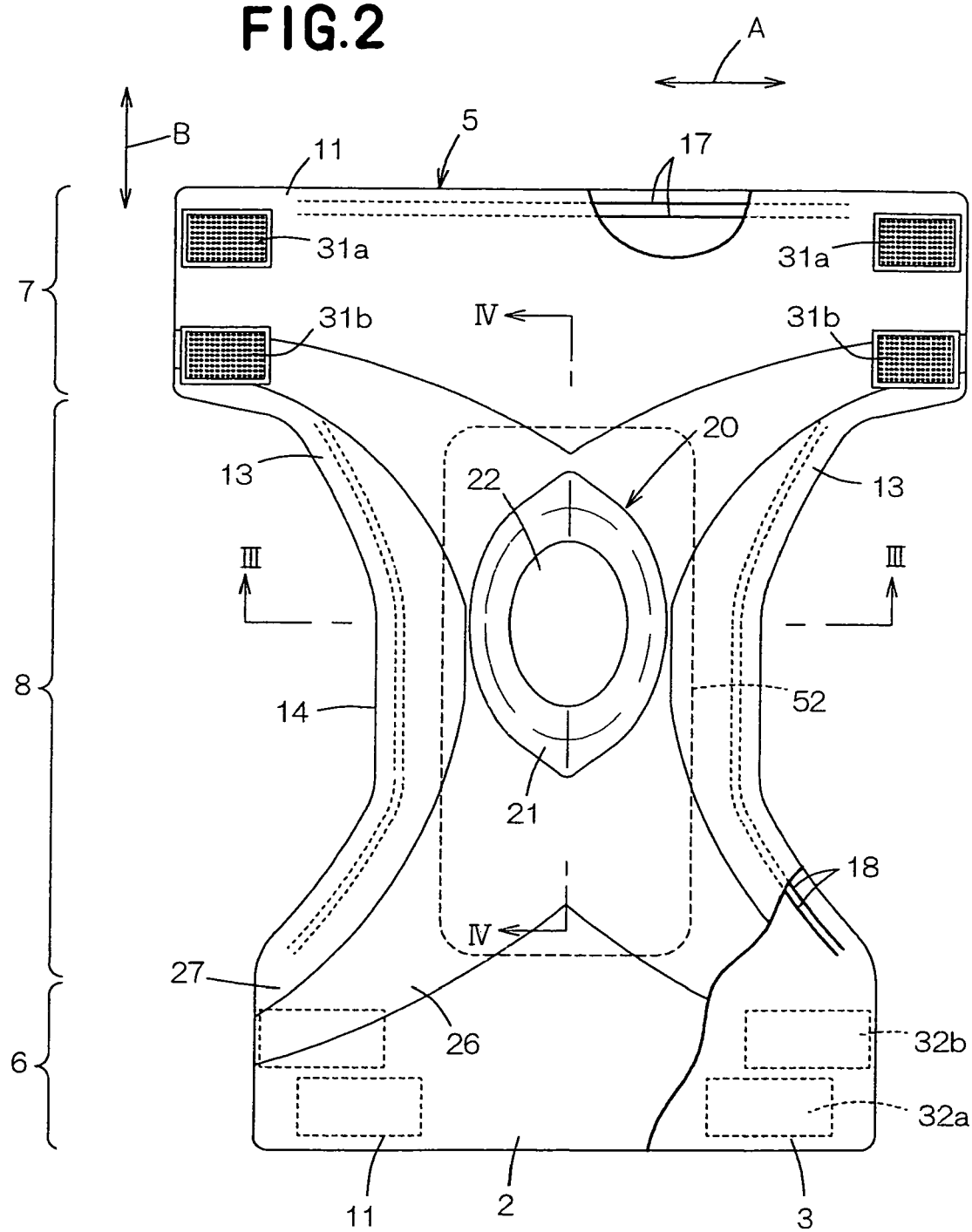
FIG. 2 is a partially cutaway plan view showing the diaper of FIG. 1.

FIG. 1 is a perspective view showing a disposable diaper 1 as put on a wearer's body and FIG. 2 is a partially cutaway plan view showing the diaper 1. The illustrated disposable diaper 1 is of open-type and has, as viewed in the plan view of FIG. 2, a transverse direction indicated by a double-headed arrow A and a longitudinal direction indicated by a double-headed arrow B. A waist-hole 15 and a pair of leg-holes 16 are formed as the diaper is put on the wearer's body. The diaper 1 presenting an hourglass-shape as viewed in the plan view of FIG. 2 comprises a holder member 5 which is elastically stretchable in the transverse direction A as well as in the longitudinal direction B and a bodily discharge receiving member 20 attached to the holder member 5. The holder member 5 comprises an elastically stretchable topsheet 2 facing the wearer's body and an elastically stretchable backsheet 3 facing wearer's clothes intermittently joined together by use of adhesive or welding technique. In the longitudinal direction B of the diaper 1, the holder member 5 has a crotch region 8, a front waist region 6 extending forward from the crotch region 8 and a rear waist region 7 extending rearward the crotch region 8. The holder member 5 further has front and rear end portions 11 extending in the transverse direction A and a pair of opposite side edge portions 13 extending in the longitudinal direction B wherein these side edge portions 13 extending in the crotch region 8 curve inward to define respective leg-surrounding lateral portions 14. Along the end portion 11 in the rear waist region 7 and the respective leg-surrounding side edge portions 14, a waist elastic member 17 comprising a plurality of rubber threads and leg elastic members 18 each comprising a plurality of rubber threads are interposed between the top- and backsheets 2, 3 and attached to at least one of these two sheets 2, 3 in a stretched or unstretched state. The crotch region 8 of the holder member 5 is provided in its transversely middle zone with a bodily discharge receiving member 20 comprising an annular protrusion 21 and a feces receiving space 22 surrounded by the protrusion 21. The protrusion 21 lies in a zone of the crotch region 8 located aside toward the rear waist region 7 and come in contact with the wearer's body so that the protrusion 21 may properly surround an anus as the diaper 1 is put on the wearer's body.

The holder member 5 in the diaper 1 formed in this manner comprises, as seen in the plan view of FIG. 2, a zonal high elasticity segment 26 extending from a periphery of the annular protrusion 21 toward the side edge portions 13 in the front waist region 6 as well as toward the side edge portions 13 in the rear waist region 7 so as to describe a substantially X-like shape and a low elasticity segment 27 defined by the remaining segment of the cover sheet 5 except for the high elasticity segment 26. When the diaper 1 is put on the wearer's body, a higher stretching force is necessary for the high elasticity segment 26 than a stretching force necessary for the low elasticity segment 27. The high elasticity segment 26 extends along the respective leg-surrounding lateral portions 14.

Such high elasticity segment 26 is formed by an elastically stretchable first sheet 28 (See FIG. 3) attached to an inner surface of the topsheet 2 as illustrated or interposed between the top- and backsheets 2, 3 and attached to at least one of these sheets 2, 3. This first elastic sheet 28 preferably has a stretch stress equal to or higher than those of the top- and backsheets 2, 3. It should be understood that the waist elastic member 17 as well as the leg elastic members 18 are optionally used to assist the holder member 5 to be tightly placed around the wearer's waist and thighs.

In the preferred holder member 5, the high elasticity segment 26 has a stretch stress of 0.25 N/15 mm or higher when the segment 26 is transversely stretched by 15% and a stretch stress of 0.6 N/15 mm when the high elasticity segment 26 is transversely stretched by 40%. At these stretch ratios, the high elasticity segment 26 exhibits the stretch stress corresponding to at least 1.5 times of the stretch stress exhibited by the low elasticity segment 27. The holder member 5 further comprises fastener means. Specifically, each of the opposite side edge portions 13 in the rear waist region 7 is provided with a pair of hook members 31a, 31b attached to the topsheet 2 each making one cooperating component of the mechanical fastener commonly known in the trade name of MAGIC TAPE, on one hand, and each of the opposite side edge portions 13 in the front waist region 6 is provided with a pair of loop members 32a, 32b attached to the backsheet 3 each making the other cooperating component of the mechanical fastener, on the other hand. Of these mechanical fastener components, the hook members 31b and/or the loop members 32b at least partially overlap the high elasticity segment 26.

Figure 3:
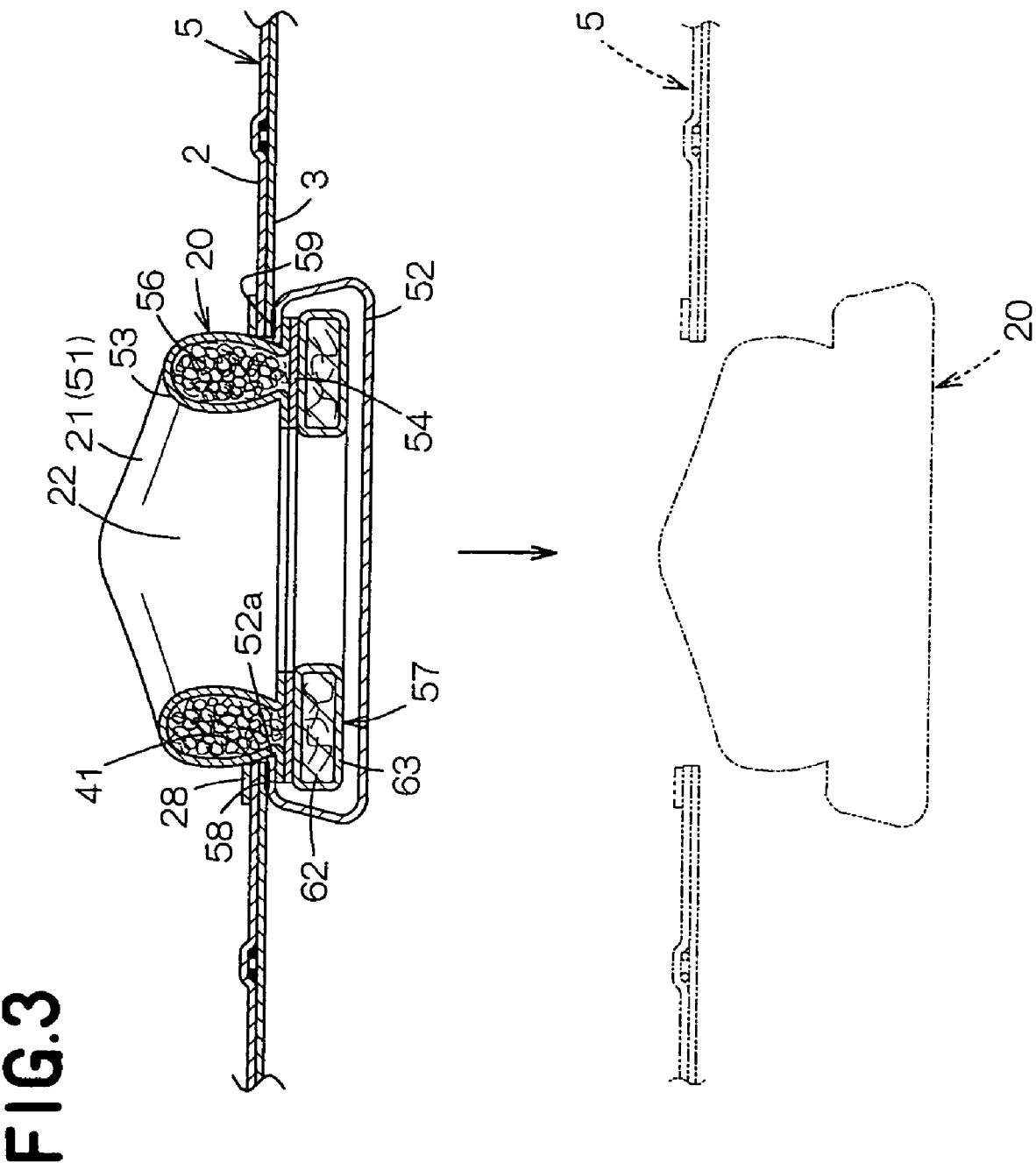
FIG. 3 is a sectional view taken along a line III-III in FIG. 2.
Figure 4:
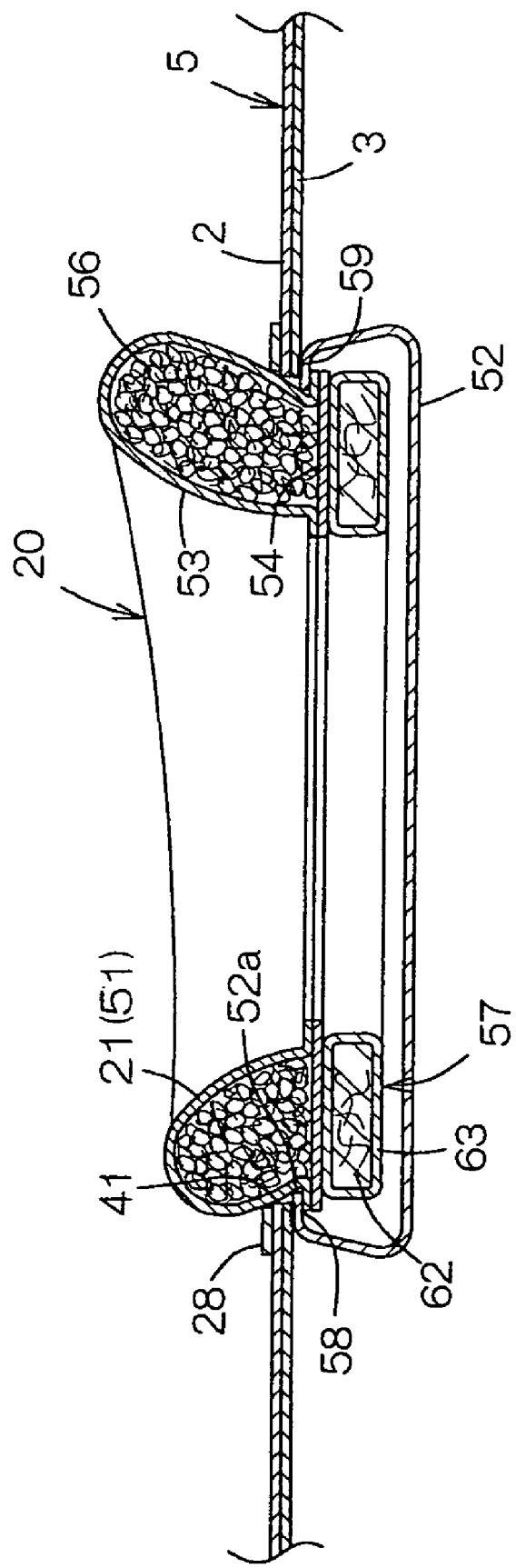
FIG. 4 is a sectional view taken along a line IV-IV in FIG. 2.

FIGS. 3 and 4 are partially cutaway sectional views taken along lines III-III and IV-IV in FIG. 2, respectively. The holder member 5 is formed in the transversely middle zone of the crotch region 8 with a through-hole 41 extending through the top- and backsheets 2, 3 as well as the first elastic sheet 28 in a thickness-direction, that is, extending between the surface facing the wearer's body defined by the topsheet 2 and the surface facing the wearer's clothes of the holder member 5. The bodily discharge receiving member 20 comprises the annular portion 51 inserted into the through-hole 41 from the surface facing the wearer's clothes of the holder member 5 to form the protrusion 21 and a bursiform portion 52 lying on the side of the surface facing the wearer's clothes.

The annular portion 51 of the receiving member 20 has a top covering sheet 53, a bottom covering sheet 54 and filler 56 filling an inner space surrounded by these covering sheets 53, 54. A liquid-absorbent block 57 lies within the inner space of the bursiform portion 52 inside the bottom covering sheet 54. The bursiform portion 52 has an opening 52a shaped substantially in coincidence with the through-hole 41 of the holder member 5 and a peripheral edge portion 58 of the opening 52a is permanently joined to the top covering sheet 53 at a lower level of the annular portion 51 by use of adhesive or welding technique, on one hand, and releasably attached to the backsheet 3 of the holder member 5 by use of pressure-sensitive adhesive, on the other hand. If the receiving member 20 is pulled down as viewed in FIG. 3 with the bursiform portion 52 peeled off from the backsheet 3, the annular portion 51 can be elastically deformed so as to be drawn off from the through-hole 41 of the holder member 5 to separate the receiving member 20 from the holder member 5 as indicated by imaginary lines in FIG. 3.

In the holder member 5, the topsheet 2, the backsheet 3 and the first elastic sheet 28 may be formed by stock material selected from the group including an elastically stretchable nonwoven fabric or woven fabric made of elastomer such as an urethane and a sheet material such as a film. The sheet material is preferably liquid-impervious and more preferably breathable and liquid-impervious. The holder member 5 is elastically stretchable in the direction indicated by the double-headed arrow A as well as in the direction indicated by the double-headed arrow B.

In the receiving member 20, the top covering sheet 53 of the annular portion 51 is hot formed from preferably a liquid-impervious, more preferably, breathable and liquid-impervious thermoplastic nonwoven fabric, woven fabric or a film. The filler 56 serving to make the annular portion 51 elastically compressive comprises a block of flexible and elastic foamed material such as a foamed polyurethane or pulverized powder of such block. Compressibility of the annular portion 51 may be controlled by mixing the pulverized powder of foam material preferably with thermoplastic synthetic fibers, more preferably with crimped thermoplastic synthetic fibers. The liquid-absorbent block 57 of the receiving member 20 may be formed by water-absorbent material 62 such as fluff pulp, super-absorbent polymer particles or super-absorbent polymer fiber or a mixture thereof, in every case, wrapped with a liquid-pervious sheet 63. Such liquid-absorbent block 57 may be replaced by liquid-absorbent sheet material having an appropriate thickness such as a pulp sheet fixed to the bottom covering sheet 54 so as to form the block 57. The bursiform portion 52 of the receiving member 20 can be formed by liquid-impervious film. A nonwoven fabric may be laminated on an outer surface of this film to provide the bursiform portion 52 with cloth-like touch. It is also possible to form the bursiform portion 52 by elastically stretchable film so that the bursiform portion 52 can bulge first when it receives bodily discharges. When the bursiform portion 52 is made of sheet material which is not elastically stretchable, the bursiform portion 52 may be previously formed with a plurality of gathers to ensure that the bursiform portion 52 bulges first when the bursiform portion 52 receives bodily discharges.

With the diaper 1 configured in this manner, even when bodily discharges flow into the bursiform portion 52, it is not likely that the holder member 5 might be contaminated with bodily discharges so far as the protrusion 21 defined by the annular portion 51 is held in tight contact with the wearer's body around the anus. It will be understood from FIG. 3 that the diaper 1 can be divided into the holder member 5 and the receiving member 20, so the holder member 5 may be washed to reuse it after the receiving member 20 contaminated with bodily discharges alone has been thrown away. The diaper 1 adapted to be used in such manner can substantially reduce a unit cost of the diaper 1 by reusing the holder member 5 compared to the conventional diaper adapted to be entirely thrown away after contaminated.

Figure 5:
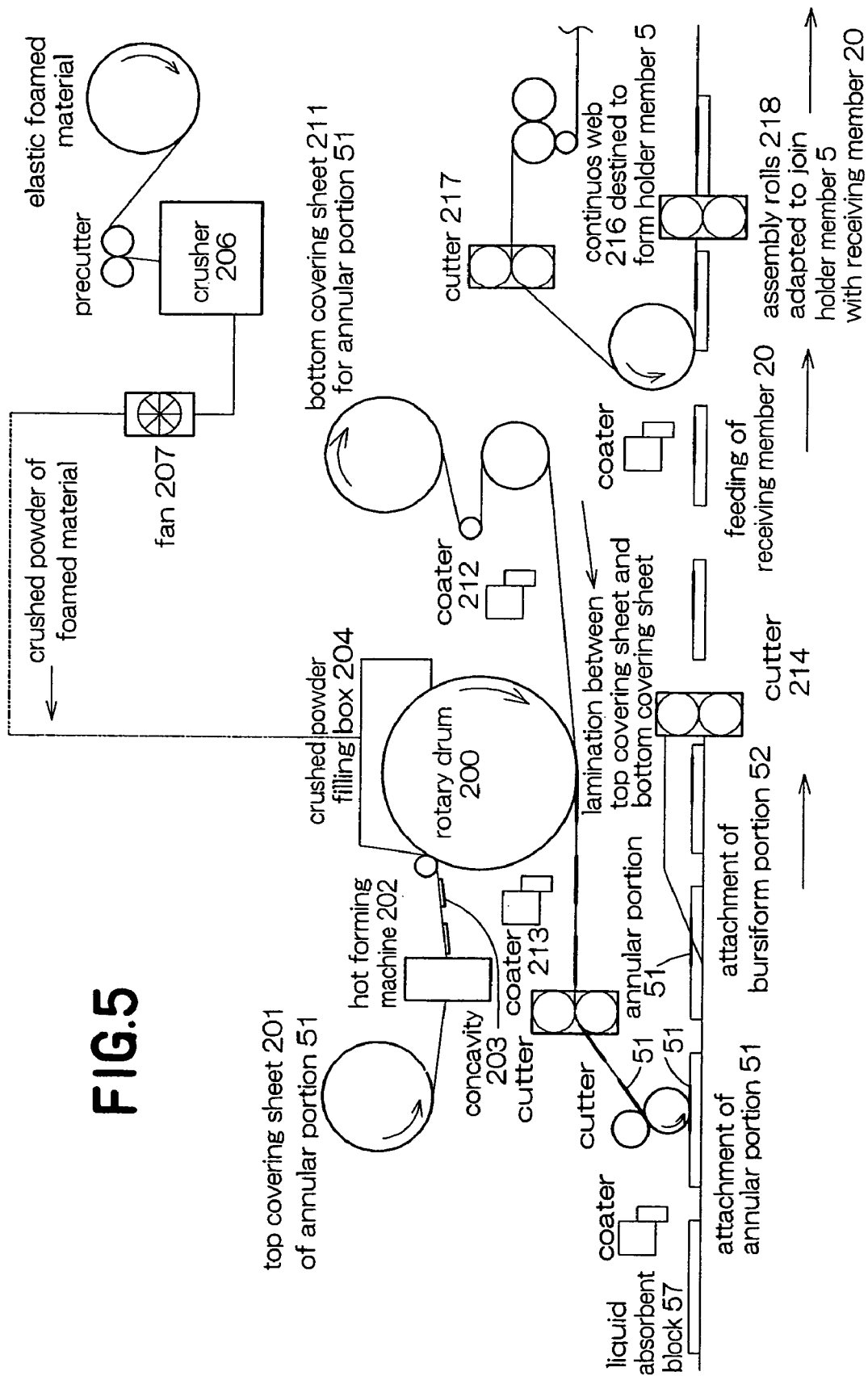
FIG. 5 is a diagram illustrating a process for continuous production of the diapers.

FIG. 5 is a diagram illustrating an example of the process for continuously making the diaper 1 shown in FIG. 2. A web 201 destined to become the top covering sheet 53 is continuously fed from upper left toward a rotary drum 200 lying at a substantially central position as viewed in the diagram. In the course of being fed toward the rotary drum 200, the web 201 passes through a hot forming machine 202 in which the web is intermittently formed with concavities 203 each corresponding to the annular portion 51. The web 201 formed with the concavities 203 in this manner is then introduced into a crushed powder filling box 204.

On the other hand, a suitable foamed material such as a foamed polyurethane destined to become the filler 56 is fed from upper right as viewed in the diagram toward the rotary drum 200. In the course of being fed toward the rotary drum 200, the foamed material passes through a crusher 206 in which the foamed material is crushed and then introduced into a filling box 204 under air blasting from a fan 207. The web 201 having the concavities 203 filled with the filler 56 in the filling box 204 is then combined with a web 211 destined to become the bottom covering sheet 54 fed toward the rotary drum 200 from right as viewed in the diagram so that the concavities 203 are successively closed with the web 211. The web 211 has previously been coated with an adhesive by a coater 212.

The liquid-absorbent blocks 57 are intermittently fed from left to right below the rotary drum 200 as viewed in the diagram and the respective annular portions 51 cut off from the webs 201, 211 bonded together are successively attached to the respective liquid-absorbent blocks 57. The respective annular portions 51 have previously been coated with an adhesive by a coater 213. The liquid-absorbent blocks 57 further run rightward as viewed in the diagram and, immediately below the rotary drum 200, the bursiform portions 52 are successively attached to the respective liquid-absorbent blocks 57. Redundant peripheral margins of the respective bursiform portions 52 are trimmed by a cutter 214 and thereby the receiving members 20 are obtained. A web 216 destined to become the holder members 5 is continuously fed from lower right with respect to the rotary drum 200 toward the web 216 cut into the individual holder members 5 by a cutter 217 so that these individual holder members 5 are assembled integrally with the individual receiving members 20 on an assembly roll 218. In this manner, the diaper 1 shown in FIG. 2 is obtained.

The present invention is applicable not only to the disposable diaper illustrated and described but also to the diaper having a pair of the annular portions 20 adapted to receive feces and urine, respectively. The diaper 1 according to the present invention is not limited to that for infants but includes diapers for adults and incontinent patient. The present invention can be implemented not only in the form of the open-type diaper 1 as illustrated but also in the form of the pull-on disposable diaper. Furthermore, it is also possible without departing from the scope of the invention to form the holder member 5 by the topsheet 2 or the backsheet 3 alone instead of by the top- and backsheets 2, 3 and the first elastic sheet 28.

The disposable wearing article according to the present invention basically comprises the holder member and the bodily discharge receiving member detachably attached to the holder member wherein the holder member is washable to be reused after detached from the contaminated receiving member. Such reusability substantially reduces a unit cost of the wearing article.

What is claimed is:

1. A disposable wearing article, comprising:
a holder member having a front waist region, a rear waist region and a crotch region extending in a longitudinal direction of said holder member between said waist regions, said holder member further having an upper surface adapted to contact a wearer's body in use and a lower surface adapted to contact said wearer's clothing in use; and
a bodily discharge receiving member removably retainable by said holder member;
wherein
said crotch region has in a transversely middle zone thereof a through-hole extending between said upper surface and said lower surface;
said receiving member comprises
an annular portion removably insertable from below said holder member through said through-hole so as to be located on the upper surface in the transversely middle zone of said crotch region for surrounding at least one of an anus and a urethral orifice of the wearer in use, said annular portion having inner and outer circumferential surfaces and a top surface connecting said inner and outer circumferential surfaces, said top surface being convex upward to define an upper circumferential edge that is rounded so as to facilitate the insertion of said annular portion from below said holder member through said through-hole; and
a discharge containing portion joined to and in fluid communication with said annular portion for receiving bodily discharges flowing through said annular portion;
when said receiving member is retained by said holder member, said annular portion is located above the upper surface whereas said discharge containing portion is positioned below the lower surface; and
said discharge containing portion comprises
a top wall having an aperture in fluid communication with the annular portion;
a bottom wall exposed on the lower surface of said holder member to an outside of said wearing article, for allowing access to and exchange of said receiving member from the outside of said wearing article;
a side wall connecting the top wall and the bottom wall; and
an absorbent core containing absorbent material.

2. The article according to claim 1, wherein the walls of said discharge containing portion are formed by a liquid-impervious and elastically stretchable sheet which renders said discharge containing portion enlargeable under a weight of the discharge received in said discharge containing portion.

3. The article according to claim 1, wherein
said annular portion includes a liquid-impervious top covering sheet bonded to the top wall of said discharge containing portion around said aperture, and flexible and elastically compressible material filled between said top covering sheet and the top wall of said discharge containing portion, and
a height of said annular portion, as measured upwardly from the top wall of said discharge containing portion, gradually increases toward at least one of longitudinally opposite ends of said annular portion.

4. The article according to claim 3, wherein said height is maximal at an apex on a longitudinal center line of said receiving member.

5. The article according to claim 1, wherein the walls of said discharge containing portion are formed by a liquid-impervious sheet which is not elastically stretchable but formed with gathers;

said liquid-impervious sheet rendering said discharge containing portion enlargeable under a weight of the discharge received in said discharge containing portion.

6. A bodily discharge receiving member for use with a holder member in a disposable wearing article, the holder member having a front waist region, a rear waist region and a crotch region extending in a longitudinal direction of said holder member between said waist regions, said holder member further having an upper surface adapted to contact a wearer's body in use and a lower surface adapted to contact said wearer's clothing in use, said crotch region having in a transversely middle zone thereof a through-hole extending between said upper surface and said lower surface, said bodily discharge receiving member being removably retainable by said holder member and comprising:

an annular portion removably insertable from below said holder member though said through-hole so as to be located on the upper surface in the transversely middle zone of said crotch region for surrounding at least one of an anus and a urethral orifice of the wearer in use, said annular portion having inner and outer circumferential surfaces and a top surface connecting said inner and outer circumferential surfaces, said top surface being convex upward to define an upper circumferential edge that is rounded so as to facilitate the insertion of said annular portion from below said holder member through said through-hole; and a discharge containing portion joined to and in fluid communication with said annular portion for receiving bodily discharges flowing through said annular portion;

wherein when said receiving member is retained by said holder member, said annular portion is located above the upper surface whereas said discharge containing portion is positioned below the lower surface; and said discharge containing portion comprises a top wall having an aperture in fluid communication with the annular portion;

a bottom wall adapted to be exposed on the lower surface of said holder member to an outside of said wearing article, for allowing access to and exchange of said receiving member from the outside of said wearing article;

a side wall connecting the top wall and the bottom wall; and an absorbent core containing absorbent material, and said annular portion comprises:

a liquid-impervious top covering sheet defining said inner and outer circumferential surfaces as well as said top surface, said liquid-impervious top covering sheet being bonded to the top wall of said discharge containing portion around said aperture; and flexible and elastically compressible material filled between said top covering sheet and the top wall of said discharge containing portion.

7. The receiving member according to claim 6, wherein the walls of said discharge containing portion are formed by a liquid-impervious sheet which is elastically stretchable;

said liquid-impervious sheet rendering said discharge containing portion enlargeable under a weight of the discharge received in said discharge containing portion.

8. The receiving member according to claim 6, wherein said annular portion has a front end segment adapted to be adjacent said front waist region in use, and a rear end segment adapted to be adjacent said rear waist region in use, wherein a height of said annular portion, as measured upwardly from the top wall of said discharge containing portion, gradually increases from the front end segment towards the rear end segment.

9. The receiving member according to claim 8, wherein said height is maximal at an apex of the rear end segment on a longitudinal center line of said receiving member.

10. The receiving member according to claim 6, wherein the walls of said discharge containing portion are formed by a liquid-impervious sheet which is not elastically stretchable but formed with gathers;

said liquid-impervious sheet rendering said discharge containing portion enlargeable under a weight of the discharge received in said discharge containing portion.

* * * * *